United States Patent
Smiley

(10) Patent No.: US 6,746,608 B2
(45) Date of Patent: Jun. 8, 2004

(54) USE OF ADSORBENT POLYMER PARTICLES IN DNA SEPARATION

(75) Inventor: Leonard H. Smiley, Philadelphia, PA (US)

(73) Assignee: Prometic Biosciences, Inc. (CA)

( * ) Notice: Subject to any disclaimer, the term of this patent is extended or adjusted under 35 U.S.C. 154(b) by 0 days.

(21) Appl. No.: 10/317,980

(22) Filed: Dec. 12, 2002

(65) Prior Publication Data

US 2003/0162853 A1 Aug. 28, 2003

Related U.S. Application Data

(63) Continuation-in-part of application No. 09/980,901, filed as application No. PCT/CA00/00701 on Jun. 12, 2000, now Pat. No. 6,573,307, said application No. 10/317,980, is a continuation-in-part of application No. PCT/GB01/02576, filed on Jun. 12, 2001.

(30) Foreign Application Priority Data

Dec. 19, 2001 (GB) ............................................. 0130333

(51) Int. Cl.[7] ........................ B01D 15/00; B01D 15/08; C02J 1/02
(52) U.S. Cl. ....................... 210/656; 210/661; 210/679; 536/127; 521/145
(58) Field of Search ................................ 210/656, 661, 210/679; 536/127; 521/145

(56) References Cited

U.S. PATENT DOCUMENTS

| | | | |
|---|---|---|---|
| 3,985,632 A | 10/1976 | Rembaum et al. | |
| 4,035,316 A | 7/1977 | Siao et al. | |
| 5,607,467 A | 3/1997 | Froix | |
| 6,046,248 A | 4/2000 | Lowe et al. | |
| 6,573,307 B1 | 6/2003 | Smiley et al. | |
| 2003/0069413 A1 * | 4/2003 | Pai et al. | |

FOREIGN PATENT DOCUMENTS

| | | |
|---|---|---|
| EP | 0 281 366 A | 9/1988 |
| EP | 0 298 503 A | 1/1989 |
| EP | 0 648 777 A | 4/1995 |
| WO | WO 00/77081 | 12/2000 |
| WO | WO 01/96556 A1 | 12/2001 |

OTHER PUBLICATIONS

Database Biosis Online!, Biosciences Information Service, Philadelphia, PA, US; Nov. 1998, Kapustin, D.V. et al. "Composite fluoropolymer–containing sorbents for isolation and purification of biopolymers" Database accession no. PREV199900110788, abstract and Bioorganicheskaya Khimiya, Nov. 11, 1998, vol. 24, No. 11, pp. 868–876, ISSN: 0132–3423.

Sawai, H. "Preparation of Several Types of RPC–5–Like Resins and Their Use for the Separation of Oligonucleotides and Mononucleotides by High–Performance Liquid Chromatogrpahy" *Journal of Chromatography* 481:201–210.

* cited by examiner

*Primary Examiner*—Morton Foelak
(74) *Attorney, Agent, or Firm*—Saliwanchik, Lloyd & Saliwanchik

(57) ABSTRACT

The invention is directed to fluorinated particles having adsorbent properties for superior performance as the stationary phase for use in chromatographic separations. In particular, the fluorinated surface of such particles of the invention presents unusual and unexpected polarity that is beneficial in performing chromatographic separations such as that used for DNA.

20 Claims, No Drawings

USE OF ADSORBENT POLYMER PARTICLES IN DNA SEPARATION

CROSS-REFERENCE TO RELATED APPLICATIONS

This Application is a continuation-in-part of application Ser. No. 09/980,901, filed Apr. 15, 2002, now U.S. Pat. No. 6,573,307 which is 371 of PCT/CA00/00701, filed Jun. 12, 2000, and of PCT/GB01/02576, filed Jun. 12, 2001.

FIELD OF INVENTION

The invention relates to the use of fluorine-containing polymer adsorbent particles as a stationary phase for carrying out chromatographic separations.

BACKGROUND OF THE INVENTION

Support materials for use in high productivity liquid chromatography must be mechanically strong in order to withstand operation at high rates of flow under high pressures. Moreover, they must be stable over the wide range of pH to which such materials are subjected during normal operation and regeneration. The stability of the polymeric particles in their environment allows them to withstand degradation and decomposition. Physical properties of particular importance to chromatographic media are (1) sphericity of the particles, (2) high surface area; (3) high pore volume and availability; (4) wide range of pore diameters, and (5) wide range of particle diameters.

U.S. Pat. Nos. 5,438,129 and 5,625,054 disclose fluorinated silica for DNA separation.

Reverse phase chromatography involves the use of a relatively non-polar stationary phase in conjunction with a very polar mobile phase that is usually water. This technique is used to separate solutes of lower polarity. Reverse phase chromatography is usually performed using silica that is coated with an organic silane to provide hydrophobicity. However, the hydrophobised silica has a severe limitation in that it cannot be used at a pH greater than 8 and cannot be cleaned with concentrated caustic soda solutions without dissolving the particles.

SUMMARY OF THE INVENTION

The invention is directed to fluorinated particles having adsorbent properties for superior performance as the stationary phase for use in chromatographic separations. In particular, the fluorinated surface of such particles of the invention presents unusual and unexpected polarity that is beneficial in performing chromatographic separations such as that used for DNA.

Further, it has been found that one can place fluorinated coatings on substrates and the resultant composition will separate super-coiled DNA from a lysed plasmid containing RNA, proteins and endotoxins, e.g. when ion-pairing chromatography is employed. These substrates can be inert materials such as glass beads or silica or polymers. Any fluorinated surface will behave in a similar manner. These surfaces can be glass spheres, fluorinated films, porous fluorinated membranes, a porous monolith or any other suitable material.

One method of making the chromatographic medium is to synthesize a fluorinated chlorosilane and react that silane with the surface of a material such as silica. The resultant medium can then be used in an ion-pairing chromatography mode to adsorb and de-sorb supercoiled DNA.

The present invention provides uses for particles as a stationary phase in chromatographic techniques. Particles of the invention are particularly suited to use where the sample to be chromatographed is a macromolecule containing nucleotides, nucleosides or polypeptides, such as DNA, RNA or endotoxins.

More particularly, after a plasmid is lysed with caustic, the resultant mixture may contain DNA, RNA, endotoxin and proteins. If the mixture is allowed to flow through a bed of a fluorinated particles, the DNA components are adsorbed onto the polymer. If the polymer is then treated, e.g. with an aqueous solution of an ion-pairing agent at the appropriate pH, typically using an appropriate buffer, pure supercoiled DNA can be preferentially eluted.

Particular aspects of the invention are as follows:

1. The use of fluorinated surfaces to isolate DNA from a lysed plasmid.
2. The use of a fluorosilane on silica.
3. The use of a fluorosilane on glass beads.
4. The use of a fluorinated membrane.
5. The use of fluorinated materials to reduce endotoxin in DNA.

DESCRIPTION OF PREFERRED EMBODIMENTS

A preferred process for the preparation of porous spherical particles of fluorinated polymer adsorbent comprises the steps of:

(1) forming a water-insoluble solution of organic compounds comprising a monomer selected from $C_{2-4}$ alkylene glycol esters of a $C_{3-6}$ acrylic acid or divinyl benzene, a polyfluorinated vinyl monomer; a free radical initiator; and a water-insoluble, organic solvent-soluble porogenic material, the weight ratio of the comonomers to porogenic material being from 0.5:1 to 2:1;

(2) forming a dilute solution of a dispersing agent in water from which any oxygen has been purged with inert gas, (3) with agitation and inert gas purging, rapidly dispersing the water-insoluble solution of organic compounds from step (1) into the dilute aqueous solution from step (2) and, as necessary, adjusting the temperature of the dispersion to 30–90° C. to initiate copolymerization of the monomers, the level of mixing energy being sufficient to disperse the water-insoluble solution of organic compounds in the solution from step (2) in the form of liquid droplets having an average diameter of no more than 10–300 µm, at least 90% of the droplets being within 40% above or below the average mean particle diameter, (4) continuing the agitation and oxygen purging of the dispersion from step (3) for a time sufficient to effect complete copolymerization of the monomers and particulation of the droplets in the form of finely divided polymer particles by precipitation of the copolymer therein;

(5) separating the finely divided copolymer particles from the polymerization reaction medium;

(6) extracting the porogenic material from the separated copolymer particles of step (5) by washing the particles with inert organic solvent, thereby forming pores within the copolymer, and (7) drying the porous copolymer particles.

Another preferred process for the preparation of porous spherical particles of fluorinated polymer adsorbent comprises the steps:

(1) forming a water-insoluble solution of organic compounds comprising (a) a monomer selected from $C_{2-4}$ alkylene glycol esters of a $C_{3-6}$ acrylic acid and a divinyl benzene, (b) a polyfluorinated vinyl monomer; (c) a monomer selected from acrylic acid, methacrylic acid and esters thereof; (d) a free radical initiator; and (e) a water-insoluble, organic solvent-soluble porogenic material, the weight ratio of comonomers (a) plus (b) plus (c) to the porogenic material being from 0.5:1 to 2:1, (2) forming a dilute solution of a dispersing agent in water from which any oxygen has been purged with inert gas;

(3) with a agitation and inert gas purging rapidly dispersing the water-insoluble solution of organic compounds from step (1) into the dilute aqueous solution from step (2) and, as necessary, adjusting the temperature of the dispersion to 30–90° C. to initiate copolymerization of the monomers, the level of mixing energy being sufficient to disperse the water-insoluble solution of organic compounds in the solution from step (2) in the form of liquid droplets having an average diameter of no more than 10–300 $\mu$m, at least 90% of the droplets being within 40% above or below the average mean particle diameter, (4) continuing the agitation and oxygen purging of the dispersion from step (3) for a time sufficient to effect complete copolymerization of the monomers and particulation of the droplets in the form of finely divided polymer particles by precipitation of the copolymer therein;

(5) separating the finely divided copolymer particles from the polymerization reaction medium, (6) extracting the porogenic material from the separated copolymer particles of step (5) by washing the particles with inert organic solvent, thereby forming pores within the copolymer, and (7) drying the porous copolymer particles.

High quality adsorbent fluoropolymer particles may be made by suspension polymerizaton with an aqueous solution containing a conventional dispersing agent. The basic components of the process are (1) the water-insoluble polymerization system, which is comprised mainly of a polyfluorinated monomer, two or more ethylenically unsaturated monomers and a free radical-initiating catalyst, and (2) the dispersion medium, which is a dilute aqueous solution containing a conventional dispersing agent. By water-insoluble solution is meant a solution sufficiently water-insoluble to permit suspension polymerization to occur. Preferred ethylenically unsaturated monomers are monomers having divinyl functionality. Non-fluorinated monomers having divinyl functionality are more preferred.

A. Dispersing Agents

The polymerization of the polyfluorinated copolymer for use in the invention is conducted in the presence of a dilute aqueous solution containing a dispersing agent, for example polyvinyl alcohol (PVA) or polyvinyl pyrrolidone. The principal function of the dispersing agent is to adjust the interfacial surface tension between the finely dispersed water-insoluble polymerization components and the continuous aqueous medium phase. By regulating the concentration of dispersing agent dissolved in the aqueous medium, the droplet size of the dispersed polymerization system and thus the size of the resultant polymerized particles can be more finely controlled.

So long as the dispersing agent is essentially completely dissolved in the aqueous medium, a wide range of molecular weights of the dispersing agent may be used successfully in the practice of the invention. One preferred dispersing agent is PVA that is at least 80% hydrolyzed, and more preferably at least 86% hydrolyzed, with a molecular weight of at least about 1,000. The maximum usable molecular weight is a function of the ambient water solubility of the dispersing agent. For example, the molecular weight of the PVA used will ordinarily not exceed 150,000 and preferably is no higher than 100,000.

For the purposes of the invention, the concentration of PVA in the aqueous medium should be within the range of 1 to 50 mL PVA per litre of water. Below 1 mL/L the modifying effect of the PVA is insufficient and above about 50 mL/L no further advantage is discernible. It is, of course, desirable to use lesser amounts of PVA in order to avoid energy-wasting increases in viscosity of the aqueous medium.

B. Polymerization System

1. Polyfluorinated Monomer: As set out above, the fluorine-containing comonomer must contain a plurality of fluorine (F) substituents. It is preferred that the fluorinated comonomer contains at least three F substituents. In addition to these restrictions on its degree of fluorination, it is essential that the fluorinated comonomer be essentially completely insoluble in water under the polymerization temperatures encountered and essentially completely soluble in the other components of the dispersed polymerization system.

Suitable polyfluorinated comonomers are those containing active vinyl sites such as acrylates, methacrylates, vinyl compounds, maleates and itaconates. Among the many other compounds useful are pentafluorostyrene, bishexafluoroisopropyl itaconate, bis-hexafluoroisopropyl maleate, heptadecafluorodecyl acrylate, perfluorooctyl methacrylate, 2,2,3,3-tetrafluoropropyl methacrylate, mono-trifluoroethyl itaconate, 2,2,2-trifluoroethyl maleate, vinyl benzyl perfluoroctanoate and vinyl trifluoroacetate.

2. Vinyl Comonomers: It is preferred that the comonomer component of the polyfluorinated copolymer for use in the invention be a non-fluorinated $C_{2-4}$ alkylene glycol ester of a $C_{3-6}$ acrylic acid (the cross-linking comonomer). The cross-linking comonomer must have at least two vinyl groups. Suitable comonomers having this composition are ethylene glycol dimethacrylate, 1,3-propylene glycol dimethacrylate, 1,4-butanediol dimethacrylate, ethylene glycol itaconate, ethylene glycol diacrylate, and ethylene glycol dimaleate. Divinylbenzene can also be used for this purpose.

A mixture of non-fluorinated comonomers can also be used, where one non-fluorinated comonomer has at least two vinyl groups, ie. the cross-linking comonomer, and the third monomer, ie. a co-monomer (c), is acrylic acid, methacrylic acid, or an ester of acrylic or methacrylic acid. Typical esters are the methyl, ethyl and hydroxyethyl esters of these acids, epoxide-containing esters of these acids and amine esters of these acids. Thus, a fourth co-monomers selected from co-monomers (c) may be used in the synthesis.

The presence of a co-monomer (c) facilitates the attachment of ligands for use in chromatographic separations by obviating the use of PVA as a linker, as described in U.S. Pat. Nos. 5,773,587 and 6,046,246, between the perfluorinated particle and the ligand. The addition of monomer (c) has little effect on the properties of the improved particles of the invention, such as stability of the particle or pore size.

Between 1 and 30% of the cross-linker ethylene glycol dimethacrylate can be replaced with a third or fourth monomer selected from co-monomers (c). These co-monomers can be chosen depending on the functionality desired. For example, functional esters of acrylic and methacrylic acid can be added such as those containing hydroxyl, epoxide, amine, quaternary ammonium, sulphonic acid etc. can be used.

3. Free Radical Initiator: An essential component of the polymerization is a source of free radicals. In particular, the system must contain one or more compounds that thermally decompose under the conditions of polymerization to form free radical species. A preferred free radical agent is a mixture of azobisisobutyronitrile (AIBN) and benzoyl peroxide (BPO). An amount of from about 10 to about 50 mg/L is suitable for this purpose. It is recognized that higher concentrations are operable functionally. However, it is preferred to use as small amounts as possible, in order to minimise the amount of extraneous materials in the formed polymer particles.

C. Porogen

Suitable porogenic materials are those organic compounds which are (1) chemically inert with respect to the other components of the polymerization phase, (2) completely soluble in the polymerization system, (3) completely insoluble in the continuous aqueous phase and (4) readily extractable from the polymerized particles at relatively low temperatures with a low molecular weight organic solvent. Dibutyl phthalate, which is easily removed by washing the polymer particles with dichloromethane, is a preferred porogen for use in the invention. Other suitable porogens include toluene, isopropyl benzene, 2-methyl-4-pentanone, 2-methyl-4-pentanol and chlorobenzene.

D. Polymerization Procedure

The polymerization should be conducted in the essentially complete absence of air or any other source of oxygen contamination, which might lead to adverse reactions with any of the components of the polymerization system, especially the monomers, crosslinking agent and free radical initiator. It has been found that the most practical way of removing and preventing the introduction of oxygen into the polymerization system is continuously to purge the polymerization reaction system before, during, and after completion of the polymerization process with an inert gas. Any of the inert gases are, of course, suitable for this purpose. However argon and nitrogen are the least expensive and will be preferred in most instances. Because the polymerization is conducted under very high energy mixing conditions, the method of introducing the purging gas is not particularly critical, so long as it is adequate in volume.

The dispersing agent functions principally for more precise control of interfacial tension between the dispersed monomer droplets and the aqueous continuous medium. The droplet size is controlled more dominantly by the amount of mixing energy used to disperse the polymerization system. Thus, only comparatively low concentrations of PVA as dispersing agent are required in the aqueous medium, e.g., on the order of 1–100 g/L. A PVA concentration within the range of 0.5–40 g/L is preferred. Though higher concentrations can be used, they do not improve functionality. Because of the necessity of forming very small droplets during the polymerization, it is, of course, desirable to avoid higher PVA concentrations which would render the aqueous medium more viscous.

The amount of energy input into the polymerization is primarily a function of the polymer particle size that is desired. Thus, if larger particles are sought, the degree of mixing (energy input) is lowered. If smaller particles are sought, the degree of mixing is raised. It is preferred that droplet size during polymerization be controlled to obtain polymer particles within the range of 5–300 $\mu$m, 20–100 $\mu$m being especially preferred F. Particle Properties Ideal chromatography media need to have the following properties: (1) spherical shape; (2) high surface area; availability of a wide range of (3) pore diameters and (4) particle diameters; (5) high pore volume, (6) high mechanical strength; and (7) both chemical and mechanical stability throughout the pH range to which the media are exposed in use.

Sphericity of the particles, rather than irregular, granular shapes, is advantageous for providing minimum resistance to flow through a packed bed of the particles and minimum back-pressure. Such regularly shaped particles are less likely to undergo densification during use.

The fluoropolymer that is used in the invention may be of the spherical type, for example as disclosed above. However, any form of fluoropolymer that has adsorbent properties can be used, whether in spherical, granular or other form. If desired, a mixture of spherical and granular fluoropolymer particles may be used, e.g. a mixture comprising 10–90% by weight of each type. It appears that such a mixture may have the effect of optimising the yield of the DNA and chromatographic flow time.

Particle size and size distribution are also important properties of the particles of the invention. In general, particles larger than about 20 $\mu$m facilitate lower back-pressure in packed columns. Moreover, the chromatographic peak width and peak shape obtained with larger particles are usually wider than the peak width and shape obtained with particles in the range of 3–15 $\mu$m. Narrow peak shapes are frequently desired for many types of separations.

The available surface area of polyfluorinated particles produced by the method of the invention is ordinarily preferred to be at least about 200 $m^2/g$ in order to obtain higher loading of antigens on the particulate medium. Nevertheless, media having much lower surface areas can readily be made according to the invention by changing the amount of porogen used in the polymerization system and decreasing the size of the particles. Concomitantly, a large pore volume of at least 0.5 mL/g is needed in order to obtain a high surface area.

A wide range of pore sizes must be available for different chromatographic procedures. Large pores are needed for the efficient capture of larger molecules, such as proteins, while small pores are needed for the efficient capture of small molecules. In general, the range of pore sizes may extend from below 60Å to as high as 1,000Å, greater than 1000Å being preferred. This range of sizes is quite readily available using the invention method of adjusting the relative amount and type of porogen within the formed polymer particles. If pores are not available, it is desired that the surface of the fluorine-containing particle be of rough texture to facilitate the entanglement of the DNA on the surface.

Because of the wide range of pH values at which chromatography media are used and because of the very high pH ranges that are encountered frequently to clean and regenerate them, it is necessary that they be chemically inert throughout the entire range of such pH exposures. In particular, chromatographic media must be able to withstand the high pH (12 or higher) encountered by the use of NaOH for cleaning the media particles, typically 0.1–1 normal.

G. Uses of the Particles

The adsorbent particles of the invention are quite versatile and may be used as the stationary phase for carrying out a wide variety of chromatographic separations. Examples of the chromatographic separations contemplated include reverse-phase separations, affinity separations, expanded bed separations, ion-exchange chromatography, gel filtration, chromatographic component separation, solid phase extraction, filtration and other recognised technical methods of distinguishing, measuring or collecting components of a chemical, biological or physical mixture. The particles may be used as support for grafting different types of ligands. Certain of the particles are particularly suited to use where the sample to be chromatographed is DNA, RNA or polypeptides.

The polyfluorinated particles of the invention can be used for chromatographic separations without a coating of a hydrophilic polymer, such as PVA.

The surface of the uncoated particles of Examples 3 and 4 is hydrophobic, but with a slight polarity. It is desired that the particle be have as high a fluorine density on its surface as possible and be as hydrophobic as possible. Reverse-phase chromatography involves the use of a relatively non-polar stationary phase in conjunction with a very polar mobile phase that is usually water. This technique is used to separate solutes of lower polarity. Reverse phase chromatography is usually performed using silica that is coated with an organic silane to provide hydrophobicity. However, the hydrophobised silica has a severe limitation in that it cannot be used at pH greater than 11 and cannot be cleaned with concentrated caustic soda solutions without dissolving the particles. A substantial advantage of the polyfluorinated particles of the invention is that they do not have this limitation.

The use of the uncoated invention particles for reverse phase chromatography is illustrated by Example 28 and the stability of the particles of the invention toward basic solutions is shown by the data obtained in Example 29 below.

Suitable hydrophilic polymers for use in coating the polyfluorinated particles of the invention are those which are uncharged, water-soluble, non-cyclic and have a multiplicity of hydroxyl groups. Though many several such hydrophilic polymers are useful for this particular function, PVA is preferred.

Advantageously, the polyfluorinated compounds of the invention may be used in medical devices with or without ligands on their surfaces to do separations that are not classified as chromatographic. For example, components of blood can be separated using a medical device in which the blood is pumped through a cartridge extra-corporeally and returned to the body. A component such as a toxin would be removed and not returned to the body.

Due to the stability of the polyfluorinated particles of the invention, sterilization can be done by gamma irradiation without destroying the particle. This property makes the particles particularly well suited for uses in medical devices that must be sanitized.

A preferred feature of the present invention is the use of an ion-pairing component. This component has the function of neutralising the charge of the moiety to be separated as well as the particulate medium, thereby allowing the interaction of the two to function in a type of reverse phase separation. Suitable ion-pairing components are well known to those skilled in the art. Ion-pairing agents that can be used are triethylamine salts such as the acetate, tetrabutylammonium ion, e.g. as the phosphate or acetate, dodecylsulfate ion and tetraoctylammonium ion.

In a preferred embodiment of the present invention, polar components are absent, or at least substantially absent. Thus, for example, the materials used in the invention preferably contain minimal or no polar groups such as hydroxyl, carbonyl or acidic functionality.

H. Derivatization of Particles

If desired, PVA-coated polyfluorinated particles, e.g. of Examples 5 and 6, can be functionalized by reacting suitable molecules with the hydroxyl groups of the PVA. Thus, strong cationic ion-exchange functionality can be provided to the particle surfaces by placing sulfonic acid groups on the surface. Likewise, strong anionic ion-exchange functionality can be provided by applying quarternary amines. Weak cation functionality can be produced by the use of carboxylic groups and weak anion functionality can be obtained by the use of primary amines.

EXAMPLES

Example 1

Production of a Porous Copolymer of Ethylene Glycol Dimethacrylate, Pentafluorostyrene and Hydroxyethyl Methacrylate 490 mL of distilled water was placed in a vessel and agitated with a high efficiency paddle mixer at 800 rpm. With continuing agitation, argon gas was added to purge oxygen from the water and 3.9 g PVA was added to the water. Agitation and purging were continued for 30 minutes, during which vortexing of the mixture was reduced by changing the angle of the agitator. Ethylene glycol dimethacrylate (50.1 g), pentafluorostyrene (39.8 g) and hydroxyethyl methacrylate (5.6 g) were mixed together and 127 mL of dibutyl phthalate were added to the mixture after which 0.48 g AIBN and 0.45 g BPO were added. The mixture was then stirred until homogeneous. The homogeneous mixture was then added rapidly to the aqueous PVA solution and the resultant polymerization mixture was heated to about 80° C. Agitation at 800 rpm and argon purging were continued throughout until the polymerization was complete.

Upon separating the formed fluoropolymer particles from the polymerization medium, they were washed sequentially with (1) 200 mL of distilled water at 60° C., (2) 200 mL of acetone at 60° C. and (3) 200 mL of a 30/70% by volume mixture of hot water and acetone at 70° C. Upon completion of the washing steps, the particles were dried overnight in an oven at 70° C.

The washed and dried fluoropolymer particles were then refluxed with 10% wt dichloromethane for 6–7 hours at 50° C. to remove the porogenic material from the particles. The porogen-free particles were placed on a sintered glass funnel and rinsed with 50 mL of acetone per gram of particles, after which the rinsed particles were dried overnight at 70° C.

The washed polyfluorinated particles had an average particle size of 51 μm, surface area of 300 m$^2$/g and pore volume of 1.0 mL/g. This procedure was very effective in making porous, spherical beads that would withstand pressure of 2000 psi in a chromatographic separation.

Example 1A

Variation of Example 1

Variations of this Example were also performed, as follows. A porous copolymer of divinylbenzene and pentafluorostyrene and epoxy ethyl methacrylate was prepared by adding to 490 ml of distilled water nitrogen gas over a 30-minute period to purge the oxygen from the water. Polyvinyl alcohol (3.9 g) was added. Pentafluorostyrene (30.9 g), divinylbenzene (35.7 g), epoxy ethyl methacrylate (20.0 g) and dibutyl phthalate (127 ml) were mixed together in a separate vessel. AIBN (0.40 g) and BPO (0.30 g) were added to the mixed monomers. The mixture of the monomers and the peroxide catalysts was added to a stirred mixture of the water and PVA. The mixture was heated to 80° C. with agitation of 800 rpm from a motor-driven, stirring paddle. The mixture was allowed to polymerize over a 4-hour period after which the polymerization was considered complete. The polymer particles were separated from the water and washed and dried. The porogen was removed as described above.

The polymerization was conducted as in Example 1, except that polyvinyl pyrrolidone was substituted for the PVA dispersing agent. The polymerization proceeded as in Example 1, only the particles were more finely divided after drying. In Example 1, the particles often clumped together on drying but were easily broken apart by mechanical or ultrasonic methods. The use of polyvinyl pyrrolidone prevented the clumping.

Porous, perfluorinated, ion-exchange particles can also be made by substituting a functional co-monomer for the crosslinker, ethylene glycol dimethacrylate. An example is the substitution of 20.0 g of methacrylic acid for the ethylene glycol dimethacrylate. The resulting polymer can function as a weak cation exchanger.

Example 2
Production of a Porous Copolymer of Ethylene Glycol Dimethacrylate, 2-(N-ethylperfluorooctanesulfoamido)ethyl Perfluoromethacrylate and Methacrylic Acid A porous copolymer of ethylene glycol dimethacrylate, 2-(N-ethylperfluorooctanesulfoamido)ethyl perfluoromethacrylate and methacrylic acid was prepared in the following manner.

Set-up:
  1 L. cylindrical reactor fitted with a "type E" agitator (Cole Palmer, 6 cm diameter and 10 cm height), reflux condenser, gas inlet tube and immersed temperature probe. The agitator is positioned so that its top impeller blade is located just above the level of the aqueous phase.

Aqueous phase:
  3.9 g PVA (Aldrich, 85,000 to 146,000 Daltons, 97–99% hydrolyzed) in 490 mL deionized (DI) water.

Organic phase:
  1.7 g of polystyrene (Aldrich, 90,000 MW standard)
  171 mL isopropyl benzene (Aldrich, 99%)
  68.5 g ethylene glycol dimethacrylate (Aldrich, 98%, 100 ppm methyl ether of hydroquinone (MEHQ)
  85.6 g 2-(N-ethylperfluorooctanesulphonamido)ethyl methacrylate (Monomers, Polymers and Dajack)
  17.1 g of methacrylic acid
  0.57 g AIBN (Aldrich, 99%)
  1.14 g BPO (Aldrich, 98%).

The aqueous phase was prepared by dissolving the PVA in water at approximately 50° C. The aqueous phase was charged to the reactor and sparged with nitrogen for 25 minutes.

The polystyrene was dissolved in the isopropyl benzene. The mixture of the three monomers was then added, followed by the initiators. After stirring for 1 hour, the organic phase still appeared cloudy and was added as such to the reactor. Under a nitrogen sweep, the mixture was stirred at 800 rpm and heated to 80° C. over a period of 30 minutes. Upon reaching reaction temperature, most of the organic phase agglomerated into a single mass that broke up into individual beads again after 25 minutes.

After 9 hours at reaction temperature, the system was allowed to cool, the aqueous phase siphoned out and the resin beads washed with 500 mL DI water, 500 mL acetone, 500 mL acetone water (30:70), 500 mL hot water and twice with 500 mL acetone.

After air drying, the resin weight is 168 g.

The resin is refluxed for 5 hours in 1 L methylene chloride, washed with 1 L acetone and air dried.

The washed and dried fluoropolymer particles were then refluxed with 10% wt. dichloromethane for 6–7 hours at 50° C. to remove the porogenic material from the particles. The porogen-free particles were placed on a sintered glass funnel and rinsed with 50 mL acetone per gram of particles, after which the rinsed particles were dried overnight at 70° C. The resultant porous beads had a particle size of 50 $\mu$m and a surface area of 300 m/gm.

Example 3
Production of a Porous Copolymer of Ethylene Glycol Dimethacrylate and Pentafluorostyrene A porous copolymer of ethylene glycol dimethacrylate and pentafluorostyrene was prepared according to the procedure described in Example 1, mixing together 55.7 g of ethylene glycol dimethacrylate and 39.8 g of pentafluorostyrene. No ethyl methacrylate was added to the mixture. This procedure was also very effective in making spherical porous particles of pentafluorostyrene.

Example 4
Production of a Porous Copolymer of Ethylene Glycol Dimethacrylate and 2-(N-ethylperfluorooctanesulfoamido) ethyl Perfluoromethacrylate A porous copolymer of ethylene glycol dimethacrylate and 2-(N-ethylperfluorooctanesulfoamido)ethyl perfluoromethacrylate was prepared according to Example 2, except that the organic phase was composed of:

1.7 g of polystyrene (Aldrich, 90,000 MW standard)
  171 mL isopropyl benzene (Aldrich, 99%)
  85.6 g ethylene glycol dimethacrylate (Aldrich, 98%, 100 ppm methyl ether of hydroquinone (MEHQ)
  85.6 g 2-(N-ethylperfluorooctanesulphonamido)ethyl methacrylate (Monomers, Polymers and Dajack)
  0.57 g AIBN (Aldrich, 99%)
  1.14 g BPO (Aldrich, 98%).

The procedure was very effective for making porous spherical particles.

Variations of Example 3 and 4 were performed to demonstrate the flexibility of the process in making particles of various pore morphologies, as illustrated in Table 1.

TABLE 1

| Porogen | % ethylene glycol in penta-fluorostyrene mixture | Pore Diameter A | % ethylene glycol in methacrylate mixture | Pare Diameter A |
|---|---|---|---|---|
| Toluene | 50 | 37 | | |
| Toluene | 40 | 122 | | |
| Dibutyl phthalate | 50 | 105 | 50 | 184 |
| Dibutyl phthalate | 40 | 73 | 40 | 261 |
| Dibutyl phthalate | 30 | 78 | | |
| 2-methyl-4-pentanone | 50 | 339 | 50 | 46 |

Table 1 illustrates the effect that the type and amount of the porogen selected may have in different monomer systems.

Example 5
Coating of Styrenic Fluoropolymer Particles with PVA

Using dry fluoropolymer particles prepared in the manner of Example 3, 50 g of such particles were deagglomerated by sonication in methanol for 5 minutes and soaked overnight in 150 ml of methanol. This de-agglomeration step was carried out in separate batches of 2 g resin in 20 mL methanol.

The methanol resin slurry was placed in a 3 L round bottom flask and enough methanol siphoned out so that it just covered the beads. A solution of 80 g PVA (31,000 to 50,00 Daltons, 98% hydrolyzed) in 1 L deionized water, previously prepared by dissolving the PVA at 50° C., was then added to the flask and the resulting slurry stirred at room temperature for 24 hours. After collecting a sample for PVA content analysis, the loading solution was separated from the beads by decantation. The beads were transferred to a fritted funnel and washed twice for 10 minutes with 500 mL deionized water, followed by removal of the water by suction. The water washes were combined and a sample retained for PVA content analysis. The washed beads were returned to the round bottom flask, and 1 L of deionized water was added. Stirring was resumed, and 1 mL of 50% aqueous solution of glutaraldehyde was added, immediately followed by 8 mL of 5 N aqueous HCl. After stirring for an additional 24 hours at room temperature, the beads were transferred to a fritted funnel, drained, washed three times with 1 L deionized water and set aside as a wet slurry.

This Example shows that spherical polyfluorinated particles can be readily coated with PVA.

Example 6
Coating of Styrenic Fluoropolymer Particles with PVA

Again using dry fluoropolymer particles prepared in the manner of Example 3, 50 g of the particles were soaked in methanol and coated with PVA in the manner of Example 5, except that the concentration of the PVA in the aqueous solution was raised to 20 g/L.

Example 7
Coating of Methacrylic Fluoropolymer Particles with PVA

In this Example, 50 g of fluoropolymer particle prepared in the manner of Example 4 were coated with PVA in the manner of Example 5.

Measurement of PVA Coating on Fluoropolymer Particles

The concentration of PVA was determined by measuring the absorbance of the PVA/iodine/boric acid complex measured at 690 nm and comparing it with a calibration curve prepared using standard PVA solutions. The linear range of the calorimetric assay is up to 1 mg PVA/mL. The amount of PVA adsorbed on the resin was determined by the difference of the initial coating solution concentration minus the final solution concentration. Results are reported in mg or g PVA/g dry resin.

Procedure: For a 9.31 mg/mL PVA coating solution, dilute samples 100× with distilled water. Pipette 2.0 mL of the samples prepared into the cuvette along with 0.5 mL of the 0.6M boric acid solution and 0.1 mL of the KI/I$_2$ solution. Mix and let stand in the darkness for 30+5 min. before taking the absorbance rating at 690 nm. Calculate the weight of PVA adsorbed onto the fluoropolymer beads by the following relationship:

$$mg\ PVA/g\ resin = \frac{(Ci)(Vi) - (Cf)(Vf)}{w}$$

where,

Ci=Concentration (mg/mL) of initial PVA coating solution

Vi=Volume (mL) of PVA coating solution

Cf=Concentration (mg/mL) of PVA coating solution at end of coating process

Vf=Final volume (mL) of coating solution

Vf may be greater than Vi due to a contribution from the wetting solvent w=weight (g) of dry fluoropolymer used in the coating process.

Using this method, the amount of PVA adsorbed onto the perfluorinated polymers was measured at 0.4 g PVA per g of the dry fluoropolymer prepared as in Example 5 and 1.51 g PVA per g of the dry fluoropolymer prepared as in Example 7.

This shows that the polyfluorinated polymer of the invention was well coated with PVA.

Measurement of HSA Capacity of PVA-coated Fluoropolymer Particles

Fluoropolymer prepared and coated with a high level of PVA in the manner of Example 5 was tested with respect to its human serum albumin (HSA) capacity. In particular, 4 mL of a 4 mg/mL solution of HSA in 20 mM phosphate buffer at pH 7.4 were added to 0.5 g of PVA coated beads prepared as in Example 5 and the resulting slurry rotated on a flat bed mixer for 16 hours at room temperature. The concentration of HSA in the supernatant was then determined using the Bradford assay. The amount of protein non-specifically bound to the resin, calculated by difference, was 2 mg/g dry fluoropolymer.

This shows clearly that protein will bind to the uncoated substrate more efficiently than to the corresponding coated substrate.

Fluoropolymer particles prepared and coated with a low level of PVA in the manner of Example 5 were also tested with respect to their HSA capacity by the same procedure. The amount of HSA adsorbed was determined to be 12.5 mg/g of dry resin.

This shows that when PVA is coated onto the polyfluorinated particles, it is a uniform, effective coating.

Measurement of Lysozyme Capacity of PVA-coated Fluoropolymer Particles

Fluoropolymer particles prepared and coated with a high level of PVA in the manner of Example 6 were tested with respect to their lysozyme capacity by the same procedure as for HSA capacity. In particular, 4 mL of a 4 mg/mL solution of lysozyme in 20 mM carbonate buffer at pH 9.0 was added to 0.5 g of PVA-coated beads prepared as in Example 6. The resulting slurry was rotated on a flat bed mixer for 16 hours at room temperature. The concentration of lysozyme in the supernatant was then determined based on the supernatant's adsorption at 280 nm. The amount of protein non-specifically bound to the fluoropolymer beads, calculated by difference, was 5 mg/g dry resin.

Example 8
Size Exclusion Chromatography of Proteins

A 10 mL Pharmacia HR 10/30 column was packed with fluoropolymer particles prepared as in Example 5 and equilibrated with 20 nM phosphate buffer at pH 7.0. The column void volume (Vo) was determined by measuring the elution volume (Ve) of Blue Dextran 2000 (0.5 mL injection, 4 mg/mL, 20 mM phosphate buffer at pH 7.0). 0.05 mL of a solution of 10 mg/mL each of ribonuclease A, ovalbumin and aldolase was loaded onto the column and eluted with the equilibration buffer at 0.02 mL/min. Similarly, a solution of chymotrypsinogen A and bovine serum albumin was loaded onto the column and eluted with the equilibration buffer at a flow rate of 0.02 mL/min. The elution volumes of the various proteins were measured from the chromatogram (UV detection) and their respective partition coefficients (Kav) calculated using the following equation:

$$Kav=(Ve-Vo)/(Vt-Vo)$$

where Vt is the total volume of the column

The results, summarized in Table 2 below, show the expected inverse relationship between partition coefficient and molecular weight for globular proteins.

TABLE 2

| PROTEIN | MOLECULAR WEIGHT (Daltons) | PARTITION COEFFICIENT |
|---|---|---|
| Ribonuclease A | 13,700 | 1 |
| Chymotrypsinogen A | 25,000 | 0.36 |
| Ovalbumin | 43,000 | 0.18 |
| Albumin | 67,000 | 0.13 |
| Aldolase | 158,000 | 0.07 |

Example 9
Binding of Blue Dye to PVA-coated Fluoropolymer Particles

This Example was directed to the binding of a blue dye at low concentration on PVA-coated fluoropolymer particles.

To 1 mL of PVA-coated fluoropolymer beads prepared as in Example 5 were added a solution of 50 $\mu$mol (40 mg) of Cibacron Blue F3G-A in 8.4 mL of water and 250 $\mu$L of 2M NaCl. After mixing for 30 minutes on a flat bed mixer, 500 $\mu$mol of $Na_2CO_3$ were added and the slurry tumble-mixed for 16 hours at 80° C. The beads were then washed, retaining the filtrates on a glass sinter with 50 mL each of water, 1 M NaCl, dimethylformamide, water 3% (v/v) methanol/water, water, methanol, water, 1 M NaOH and finally 100 mL fractions of water until the filtrate became clear. The amount of Cibacron Blue F3G-A bound to the resin was 15 $\mu$mol/mL, determined by measuring the dye concentration in the washing solutions, determined by adsorbance at 620 nm, and calculating the amount bound by difference.

Lysozyme Capacity of the Affinity Polymer

This test was carried out using a fluoropolymer prepared in the manner of Example 9, which contained a blue dye binding with low ligand density. A 1 mL Pharmacia HR 5/10 column was packed with a resin prepared as in Example 13 and equilibrated with sodium phosphate buffer (20 mM, pH 7.4). 4 mL of a 5 mg/mL solution of lysozyme in the equilibration buffer was loaded onto the resin at 1 mL/min. The lysozyme was then eluted from the resin using 1 M NaCl in 20 mM sodium phosphate buffer, pH 7.4. The amount of lysozyme eluted, as determined by measuring the eluent's absorption at 280 mm, was 18 mg per mL of fluoropolymer.

This result should be compared with the result where no blue dye was bonded to the PVA.

Example 10
Binding of Blue Dye to PVA-coated Fluoropolymer Particles

This Example was directed to binding Cibacron Blue F3G-A dye to a PVA-coated styrenic fluoropolymer particles with a high concentration of the blue dye. The resin was coated with the PVA in the manner of Example 6, except that the amount of water to dissolve the 50 $\mu$moles of blue dye was 1 ml. The dye was applied in the manner of Example 9.

The resulting ligand density was 25 $\mu$mol per mL of the fluoropolymer particles.

Lysozyme Capacity of the Affinity Polymer

This test was carried out using a fluoropolymer prepared in the same manner as Example 10, but having a high ligand density. The amount of lysozyme eluted was 20 mg/ml of resin.

Non-adsorption of Myoglobin

Using myoglobin as the protein, no protein adsorption by the polymer could be detected.

Bed Expansion

In this test, a 40 cm×1 cm column was packed with the fluoropolymer particles of Example 10 and subsequently screened to a 63 to 82 $\mu$m particle diameter range. Water was pumped up-flow in the column and the bed expansion ration (the ratio of the bed depth at a given flow rate vs. bed depth without flow) He/Ho, measured at various flow rates. The results are summarized in Table 3.

TABLE 3

| Flow Rate (cm/h) | 8 | 25 | 40 | 55 | 68 |
|---|---|---|---|---|---|
| Bed Expansion ration (He/Ho) | 1.2 | 1 7 | 1.75 | 1 9 | 2.1 |

These data illustrate the advantageous use of the particles having a higher density, ie. 1.2 g/mL versus only 1.09 g/mL for prior art polymeric particles.

Chemical Stability of the Resin

A series of tests was carried out to determine the chemical stability of the adsorbent resin prepared in the manner of Example 3. For this series, 200 mg of fluoropolymer particles prepared as in Example 10 were soaked in 2 mL of the solvent indicated. Leakage of the Cibacron Blue F3G-A was checked over time by monitoring the supernatant adsorbance at 620 nm. The dye concentrations measured in the supernatant after 37 days are summarized in Table 4.

TABLE 4

| SOLVENT ($\mu$mol) | DYE CONCENTRATION |
|---|---|
| 25% aq. Glycerol | 0.008 |
| 1% aq. Sodium dodecyl Sulfate | 0 008 |
| 8 M urea | 0.004 |
| 1 M NaSCN | 0.01 |
| 5 M HCl | 0.002 |
| dimethylformamide | 0 01 |
| Methanol | n d |
| Acetone | n.d |
| Water | 0 002 |

Example 11
Use of Uncoated Polyfluorinated Particles for Reverse-phase Chromatography Polymer particles prepared in the manner of Examples 3 and 4 were packed at 1,600 psi into stainless steel columns of 250 cm length and 0.46 cm inside diameter. The slurry solvent was 50/50 by volume methanol-isopropanol. The gradient test mixture solvent was 50/50 by volume acetonitrile/water with 0.1 TFA. The mobile phase was A=water with 0.1% TFA, B-acetonitrile with 0.1% TFA. The test mixture was Vitamin B-12(1.0 mg), bovine insulin (3.0 mg), ribonuclease A (3.0 mg), human albumin (3.0 mg) and thyroglobulin (3.0 mg). The retention times (minutes) comparing the effectiveness of methacrylic particles with the pentafluorostyrene polymer particles of the invention are set out in Table 5.

TABLE 5

| Solute | (Retention time, minutes) | |
| --- | --- | --- |
| | Pentafluorostyrene Polymer | Fluorinated Methacrylic Polymer |
| Vitamin B-12 | 1.00 | 1.00 |
| Bovine insulin | 1.59 | 1.75 |
| Ribonuclease A | 1.83 | 2.02 |
| Human albumin | 2.08 | 2.32 |
| Thyroglobulin | 2.40 | 2.72 |

Correlation of the data showed that smooth, symmetrical, non-overlapping curves were obtained. The data therefore clearly demonstrate that both the uncoated pentafluorostyrene polymer and the uncoated fluorinated methacrylic polymer particles are effective media for the chromatographic separation of mixtures of materials such as proteins.

The same columns were washed with 60 column volumes of 5N sodium hydroxide solution, followed by 60 column volumes of deionized water. The solutes were then reinjected and the same gradient as above was observed. In particular, the caustic-washed resin showed the same retention as the resin that had not undergone such washing, thus illustrating the robustness of the particles.

Example 12
Modification of Synthesis Variables to Produce Polyfluorostyrene Particles of Widely Different Particle Size

TABLE 6

| Particle Size, μm | 16 | 120 |
| --- | --- | --- |
| Reactants | | |
| Deionized water, mL | 660 | 490 |
| PVA, g | 16 | 3.9 |
| Pentafluorostyrene, g | 10 | 39.8 |
| Ethylene glycol dimethacrylate, g | 14 | 55.7 |

TABLE 6-continued

| Dibutyl phthalate, mL | 32 | 127 |
| --- | --- | --- |
| AIBN, g | 0.12 | 0.48 |
| BPO, g | 0.12 | 0.49 |
| Sodium lauryl sulfate, g | 0.06 | None |
| Agitator Speed, RPM | 900 | 395 |

The following Table shows a comparison between polyfluorinated adsorbents of the invention and available chromatography supports.

TABLE 7

| Matrix | Chemical Stability (pH) | Mechanical Stability | Permeability To Macro- | Non-specific Adsorption | Ease of Derivatization | Resistance of 5 N NaOH |
| --- | --- | --- | --- | --- | --- | --- |
| Agarose | 4–9 | Low | Excellent | Low | Good | Poor |
| Crosslinked | 2–14 | Low | Excellent | Low | Good | Poor |
| Crosslinked dextron | 72 | Low | Poor | Low | Good | Poor |
| Crosslinked polyacrylamide | 2–10 | Medium | Poor | Low | Good | Poor |
| Polyacrylamide/ Dextran | 3–11 | Low | Excellent | Medium | Good | Poor |
| Polyacrylamide/ Agarose | 3–10 | Medium | Good | Medium | Good | Poor |
| Crosslinked hydroxyethyl Methacrylate | 1–14 | High | Good | High | Poor | Very poor |
| silica | 2–9 | High | Good | High | Poor | Very poor |
| Polystyrene/ Divinylbenzyne | 1–14 | High | Good | High | Good | Good |
| Polyfluorinated particle of the invention with hydrophilic surface coating | 1–14 | High | Excellent | Low | Excellent | Excellent |

From the data in Table 7, it can readily be seen that the adsorbents of the invention are chemically stable over a very broad pH range and have a high mechanical stability. The novel adsorbents also have excellent permeability to macromolecules and, quite desirably, low non-specific adsorption properties. In addition, these adsorbents have excellent ease of derivatization and excellent resistance to the corrosive effects of 5N NaOH solutions. None of the other well-known adsorbents have such uniformly outstanding performance in all of the listed functionally important properties.

Example 13
A Porous Copolymer of Divinylbenzene and Pentafluorostyrene

To 490 ml of distilled water was added nitrogen gas over a 30-minute period to purge the oxygen from the water. Polyvinyl alcohol (3.9 g) was added. Pentafluorostyrene (30.9 g), divinylbenzene (55.0 g) and dibutyl phthalate (127 ml) were mixed together. AIBN (0.40 g) and PVA (0.30g) were added to the mixed monomers. The mixture of the monomers and the peroxide catalysts was added to a stirred mixture of the water and PVA. The mixture was heated to 80° C. with agitation of 800 rpm from a motor-driven, stirring paddle. The mixture was allowed to polymerize over a 4-hour period after which the polymerization was considered complete. The polymer particles were separated from the water and washed and dried. The porogen was removed as Example 1. The resulting particles were porous and had a particle size of 50 μm.

Example 14
Separation of Components of Plasmids

A plasmid (Amp-resistant) transformed host (DH5-alpha) was grown to high density in an enriched medium and the bacterial pellet was subjected to an alkaline lysis procedure. The lysate was filtered and then precipitated with 0.7 volumes of ice cold isopropyl alcohol (IPA) by centrifugation at 8000×g for 45 minutes. The liquid from the centrifugation was used as the sample to be chromatographed.

A Vantage-L series column (4.4 cm id) was packed with an ethanolic slurry containing approximately 90 ml of the particles described in Example 3 (50 μm, surface area of 300/m/gm, non-PVA coated). The column was packed at about 20 mL/min (approximately 80 cm/h linear flow rate) and operated at 16 mL/mm. Column effluent was monitored at 260 nm and the absorbance was detected on a chart recorder. The column was equilibrated with EQB (0.1 M potassium phosphate, pH 7.2 mM tetrabutylammonium phosphate (TBAP) and 1% ethanol) and the above described sample to be chromatographed (30 mg worth) was not loaded until the pH of the effluent was less than 9. The wash buffer WB1 was 93% sodium chloride/TRIS/EDTA, pH 8, and 7% ethanol. The elution buffers were the following: EL1 (elution buffer 1) was 0.1 N potassium phosphate, 2 mM TBAP, 10% ethanol; EL2 (elution buffer 2) was 0.1 M potassium phosphate, 2 mM TBAP, 12.5% ethanol, and EL3 (elution buffer 3) was 0.1 N potassium phosphate, 2 mM TBAP, 10% ethanol.

Particle Analysis

Sample 1 was collected during the load and re-equilibration step. No DNA was present on particles in the packed column.

Sample 2 was collected while WB1 was passing through the column and contained the bulk of the RNA and a small amount of nicked open circular DNA.

Sample 3 and 4 were collected during WB1. Sample 3 contained a small amount of supercoiled DNA, more nicked/open circular DNA and the last of the RNA. Sample 4 contained a small quantity of DNA.

DNA loss may be reduced by cutting back on the ethanolic content of WB1 or increasing the TBAP concentration, the latter of which is preferred since this may still allow species selectivity by ethanol concentration at Samples 4, 5 and 7.

Sample 5 (EL1) contained supercoiled DNA and trace amounts of non-supercoiled.

Sample 6 (EL2) contained the bulk of the DNA of which more than 90% was supercoiled.

Sample 7 (EL3) contained the residual DNA of which at least 25% was non-supercoiled.

95% of the DNA in the plasmid was recovered.

The amount of endotoxin in Sample 6 was measured by LAL Test (BioWhittaker) and found to be 58 EU/mg of DNA. The starting endotoxin level in the plasmid was 8000 EU/mg.

This Example shows that the use of ion-pairing chromatography with fluorine-containing particles can isolate super-coiled DNA and concurrently lower the endotoxin level in the DNA.

The RNA in Sample 2 can be further purified. This example also shows that this method and materials can also be used to isolate RNA from a plasmid.

Example 15
Use of Polyfluorinated, Granular Particles to Remove Endotoxin from DNA Six litres of LB medium spiked with Ampicillin (50 μg ml$^{-1}$) was inoculated with 2.5 ml of a seed culture of pRc/CMV-HBs(s)(ca. 5500 bp) bearing host (*E. coli* DH5α) and grown for 13 hours. The cell mass was harvested by centrifugation. The material was resuspended in 500 ml of 50 mM Tris.HCl/10 mM EDTA (pH 8) containing 100 μg ml$^{-1}$ RNaseA. An equal volume of lysis buffer (1% SDS/0.2 N NaOH) was added and the contents were mixed by inversion and allowed to stand for five minutes. Then, 125 ml of ice-cold neutralization buffer (3 M potassium acetate, pH 5.5) was added to the mixture and a white precipitate formed.

The mixture was immediately centrifuged for 20 minutes at 9,000×g (4° C.) Ice-cold 2-propanol was applied to the lysate. The mixture was spun for 15 minutes at 5,000×g (4° C.). The pellet was allowed to air dry and was then suspended in buffer A (a water solution of triethylamine acetate at pH 7.0).

Ion-pairing chromatography was performed as follows. 24 g of a granular tetrafluorinated ethylene polymer of particle size of 120 microns was placed in a column of 38 mm (1.5 inches) ID and 152 mm (6.0 inches) length with a capacity of 300 cc. The bed height was 51 mm (2 inches). The polymer was equilibrated with buffer A. Then, 40 ml of the re-suspended, lysed plasmid in buffer A was allowed to flow through the column. Then, two washes using 40 ml of buffer B were done. Buffer B contained a mixture of Tris, EDTA and sodium chloride. The column was then treated with 50 ml of buffer C. Buffer C contained sodium acetate and isopropyl alcohol.

The RNA was eluted in the first wash buffer B. No DNA was detectable in the eluent when buffer B was used. The eluent from buffer C contained the DNA in supercoiled, relaxed and linear states.

The elution fraction using buffer C was split into centrifuge tubes and precipitated using centrifugation at 8,000×g (4° C.) for 20 minutes using ice-cold, absolute ethanol. The pellets were pooled by combining them using 70% ethanol, spun briefly and then allowed to air dry. 3 ml of TE (10 mM Tris/1 mM EDTA, pH 8) were added to the pellets and they were gently agitated at room temperature to re-suspend the DNA. The DNA was then tested for composition and purity.

The quantity of the DNA was 8.4 and 9.1 mg from duplicate experiments. The purity of the DNA, as measured by ultra-violet analysis using the ratio of 260/280 nm wavelengths was 1.54 and 1.81 respectively, indicating a high level of purity. The amount of RNA in the DNA was undetectable, using a BCA assay from Pierce Chemical Corporation. The amount of endotoxin in the DNA as measured by a BioWhittaker QLC test was 58.8 EU/mg and 64.4 EU/mg in duplicate tests. The starting amount of endotoxin in the plasmid was >8000 EU/mg.

Example 16
Use of a Polyfluorinated Granular Particles to Purify DNA from RNA

A plasmid was made using the above fermentation procedure and purified using ion-exchange and size exclusion chromatography, to give DNA with a 260/250 mn ratio of 1.81 indicating that it was very pure and contained virtually no RNA. In an attempt to quantify the adsorption/desorption of DNA onto its surface, 16 g of a granular polytetrafluoroethylene homopolymer of 30 μm particle size was placed into a chromatography column. 4.0 mg of DNA described above was loaded onto the column using the procedure described in Example 15. Using the methods described in Example 15, it was found that 4.0 mg was adsorbed onto the column and 3.90 mg was eluted from the column using buffer C. This represents 97.5% of the DNA. This shows the affinity of the totally fluorinated polymer for DNA and the ability to desorb all of the DNA using ion-pairing chromatography. The flow time was 1.5 hours.

Example 17
Use of Polyfluorinated Granular Particles Containing Some Polar Groups to Purify DNA Example 14 was repeated, except that the polymer used in the column was a granular copolymer of tetrafluoroethylene and perfluoropropyl vinyl ether. The particle size was 30 µm. 82% of the DNA was adsorbed onto the column, indicating that polar groups may interfere with adsorption and desorption. The flow time was 1.5 hours.

Example 18
Use of Polyfluorinated Particles to Purify DNA

Example 3 was repeated, except that a granular copolymer (particle dimension 30 µm) of tetrafluoroethylene and hexafluoroethylene (12/1) was used in the column. In this case 58% of the polymer was adsorbed and eluted, with a flow time of 1.5 hours.

Example 19
Use of Polyfluorinated Particles

Example 3 was repeated, except that a granular copolymer (particle dimension of 30 µm) of tetrafluoroethylene and ethylene (1/1) was used in the column. In this case 39% of the DNA was adsorbed and eluted with buffer C. The flow time was 1.5 hours.

Example 20

Example 16 was repeated, except that a copolymer of ethylene glycol dimethacrylate and pentafluorostyrene (85/15 w/w) of particle size 30 µm and pore diameter of 700Å was used. 95% of the DNA was adsorbed and desorbed. The flow time was 3.25 minutes.

Example 21
Use of Particles with Small Pores to Purify DNA

Example 16 was repeated, except that spherical copolymer particles of pentafluorostyrene and ethylene glycol dimethacrylate (76/24) of particle size of 60 µm and pore size of 700Å was used. In this case only 65% of the DNA was adsorbed and desorbed, showing the effect of smaller pores. The flow time was 1.2 minutes.

Example 22
Effect of Polar Groups on the Purification of DNA

Example 16 was repeated, except that a copolymer of pentafluorostyrene and ethylene glycol dimethacrylate and hydroxyethyl methacrylate (40/28/28) was used. The spherical particle size was 60 µm and the pore size was 600Å. 15% of the DNA was adsorbed and desorbed. The flow time was 1.5 hours.

This Example indicates that polar groups and dilution of the fluorine content of the polymer have affected the purity of the DNA. This Example also shows that copolymers can be made which have the functionality for reacting with attachment ligands such as epoxide.

Example 23
Effect of Mixture of Granular and Spherical Particles in the Purification of DNA Example 16 was repeated, except that a 50/50 by weight of a mixture of the polymers in Examples 17 and 21 was used. The yield was 88.0% and the flow time was 6.93 minutes. This shows that mixtures can be used to optimize residence time and yield.

Example 24
Effect of No Fluorines on the Particle Surface in the Purification of DNA Example 16 was repeated, except that a copolymer of styrene and divinylbenzene of particle size 35 µm and 1000Å pore size (Amberchrome purchased from TosoHaas) was used. All of the DNA was absorbed onto the polymer but none could be eluted. This shows the necessity of having fluorine atoms on the polymer, in order to be able to elute DNA using ion-pairing chromatography.

Example 25
Use of a Fluorinated Surface on Small Pore Silica in the Purification of DNA A material of composition pentafluorophenylpropyldimethylchlorosilane was reacted with granular silica particles. The silica which was used had a particle size of 50 µm and a pore diameter of 150Å. 4 g of the resultant fluorinated silica material was placed in a chromatography column. Pure DNA was made according to the procedure outlined in Example 16 and loaded onto the column and eluted according to that Example. It was found that 3.99 g was adsorbed onto the column and 3.80 g were eluted from the column. The yield was 95.24%. This shows that the fluorinated silica was able to adsorb and desorb DNA when used in an ion-pairing chromatography mode.

Example 26
Effect of Variation of the Composition of the Fluorinated Silica Surface in the Purification of DNA Example 25 was repeated, except that the silane was (tridecafluoro-1,1,2,2-tetrahydrooctyl)dimethylchlorosilane. The yield of DNA was 95.0%.

Example 27
Reduction of Endotoxin in DNA Using Fluorinated Particles and Reverse-Phase Chromatography This Example shows a reduction of the level of endotoxin in DNA. To demonstrate this, a DNA solution, purified using a Qiagen Mega kit with surfactant to reduce the endotoxin, was passed over a column containing a copolymer of pentafluorostyrene and ethylene glycol dimethacrylate as described in Example 21. The starting endotoxin concentration was 45 EU per milliliter of DNA. After passing over the column containing the fluorine-containing co-polymer, the endotoxin was measured as being less than 0.01 EU per milliliter of DNA.

Example 28
Reduction of Endotoxin in DNA Using Fluorinated Particles and Reverse-Phase Chromatography Example 27 was repeated with DNA purified using a Qiagen Mega kit, but without the endotoxin-reducing surfactant in the kit. In this case, the starting endotoxin concentration was greater than 1000 EU per milliliter of DNA. After passing the DNA solution over the fluorine-containing polymer, the endotoxin level was measured at less than 0.01 EU per milliliter. This shows the effectiveness of the fluorine-containing materials in reducing endotoxin.

I claim:

1. A method for the separation of a nucleic acid in a liquid sample, comprising contacting the sample with adsorbent particles of a fluoropolymer such that the nucleic acid adsorbs to said fluoropolymer thus separating the nucleic acid from other components of the liquid sample that do not adsorb to said fluoropolymer.

2. The method of claim 1, wherein the sample comprises the lysis products of a plasmid.

3. The method of claim 1, wherein the sample contains endotoxins and DNA.

4. The method of claim 1, for separating RNA from DNA.

5. The method of claim 1, for purifying DNA.

6. The method of claim 1, conducted in the absence of a low or nil amount of polar components.

7. The method of claim 1, wherein the particles comprise granular and/or spherical particles.

8. The method of claim 1, wherein the particles are not cross-linked.

9. The method of claim 1, wherein the particles are cross-linked with divinylbenzene.

10. The method of claim 1, which is conducted in the presence of an ion-pairing component.

11. The method of claim 1, wherein the particles are fluorinated silica.

12. A method for the separation of a nucleic acid in a liquid sample, comprising contacting the sample with a fluorinated surface such that the nucleic acid adsorbs to said surface thereby separating the nucleic acid from other components of the liquid sample that do not adsorb to said fluorinated surface.

13. The method of claim 12, wherein the fluorinated surface is a fluorinated membrane.

14. The method of claim 12, wherein the fluorinated surface is on a porous monolith.

15. The method of claim 12, wherein the sample comprises the lysis products of a plasmid.

16. The method of claim 12, wherein the sample contains endotoxins and DNA.

17. The method of claim 12, for separating RNA from DNA.

18. The method of claim 12, for purifying DNA.

19. The method of claim 12, conducted in the absence of a low or nil amount of polar components.

20. The method of claim 12, which is conducted in the presence of an ion-pairing component.

* * * * *